(12) United States Patent
Clasen et al.

(10) Patent No.: US 11,324,397 B2
(45) Date of Patent: May 10, 2022

(54) SUCTION MIRROR HAVING A CENTRAL WALL

(71) Applicant: CLEVERDENT LTD., Münster (DE)

(72) Inventors: Stephan Clasen, Münster (DE); Martin Kayser, Köln NRW (DE)

(73) Assignee: CLEVERDENT LTD., Münster (DE)

( * ) Notice: Subject to any disclaimer, the term of this patent is extended or adjusted under 35 U.S.C. 154(b) by 205 days.

(21) Appl. No.: 16/474,326

(22) PCT Filed: Jan. 9, 2018

(86) PCT No.: PCT/EP2018/050467
§ 371 (c)(1),
(2) Date: Jun. 27, 2019

(87) PCT Pub. No.: WO2018/130526
PCT Pub. Date: Jul. 19, 2018

(65) Prior Publication Data
US 2019/0343378 A1  Nov. 14, 2019

(30) Foreign Application Priority Data

Jan. 10, 2017 (DE) ..................... 10 2017 000 105.7

(51) Int. Cl.
*A61C 17/08* (2006.01)
*A61B 1/247* (2006.01)
(Continued)

(52) U.S. Cl.
CPC ............... *A61B 1/247* (2013.01); *A61B 1/04* (2013.01); *A61C 17/08* (2019.05); *A61C 17/088* (2019.05)

(58) Field of Classification Search
CPC .............................................. A61C 17/06–135
(Continued)

(56) References Cited

U.S. PATENT DOCUMENTS 3,092,910 A * 6/1963 Warriner ................ A61C 17/08
433/31
3,928,916 A * 12/1975 Hansson ................ A61C 17/08
433/31
(Continued)

FOREIGN PATENT DOCUMENTS

DE 102006048463 A 4/2008
DE 102012100119 B3 12/2012
(Continued)

OTHER PUBLICATIONS

International Search Report dated May 17, 2018 re: Application No. PCT/EP2018/050467, pp. 1-3, citing: U.S. Pat. No. 3 092 910 A, EP 2 181 643 A1, GB 1 255 719 A, DE 10 2012 100119 B3, U.S. Pat. No. 5 951 284 A, US 2016/143521 A1 and DE 10 2013 110302 A1.

*Primary Examiner* — Matthew M Nelson
(74) *Attorney, Agent, or Firm* — Cantor Colburn LLP

(57) ABSTRACT

A dental suction mirror for suctioning liquids and particles from an oral cavity of a patient includes a tubular hollow main body having an inner surface, an outer surface, a longitudinal axis, and a connection opening for a tube and a suction opening. The inner surface has a mirrored surface that can be observed through the suction opening, with the mirrored surface being arranged in such a manner that the oral cavity can be observed at least in some regions via said mirrored surface. The hollow base body has a central wall along its longitudinal axis, which divides the hollow space at least in some regions into a first hollow channel and a second hollow channel.

7 Claims, 2 Drawing Sheets

(51) Int. Cl.
*A61C 17/06* (2006.01)
*A61B 1/04* (2006.01)

(58) Field of Classification Search
USPC .......................................................... 433/31
See application file for complete search history.

(56) References Cited

U.S. PATENT DOCUMENTS

| | | | | |
|---|---|---|---|---|
| 5,139,420 | A * | 8/1992 | Walker | A61C 17/0208 433/31 |
| 5,281,134 | A * | 1/1994 | Schultz | A61C 1/088 433/29 |
| 5,295,826 | A * | 3/1994 | Yandell | A61C 17/088 433/31 |
| 5,931,670 | A * | 8/1999 | Davis | A61C 1/088 433/91 |
| 5,951,284 | A * | 9/1999 | Lake | A61C 17/08 433/31 |
| 8,608,472 | B2 * | 12/2013 | Clasen | A61C 17/08 433/91 |
| 9,833,295 | B2 * | 12/2017 | Vayser | A61B 90/30 |
| 10,786,139 | B2 * | 9/2020 | Clasen | A61C 17/088 |
| 2005/0239014 | A1 * | 10/2005 | Frider | A61C 17/08 433/31 |
| 2007/0148611 | A1 * | 6/2007 | Frider | A61B 1/253 433/31 |
| 2008/0089088 | A1 * | 4/2008 | Joseph | G02B 1/048 362/573 |
| 2015/0320528 | A1 * | 11/2015 | Hirsch | A61C 17/12 433/91 |
| 2015/0374454 | A1 * | 12/2015 | Beerstecher | A61C 19/004 433/27 |
| 2016/0143521 | A1 * | 5/2016 | Watson | A61B 1/0615 433/30 |
| 2016/0227987 | A1 * | 8/2016 | Clasen | A61B 1/00094 |
| 2019/0343378 | A1 * | 11/2019 | Clasen | A61B 1/247 |

FOREIGN PATENT DOCUMENTS

| | | |
|---|---|---|
| DE | 102013110302 A1 | 3/2015 |
| EP | 2181643 A | 5/2010 |
| GB | 1255719 A | 12/1971 |
| JP | S54127488 U | 9/1979 |
| JP | 2003275176 A | 9/2003 |
| JP | 2007517554 A | 7/2007 |
| JP | 2016536087 A | 11/2016 |
| WO | 2015039752 A1 | 3/2015 |

* cited by examiner

SUCTION MIRROR HAVING A CENTRAL WALL

TECHNICAL FIELD

The present disclosure relates to a dental mirror suction device for suctioning liquids and particles from an oral cavity of a patient, with a hollow base body having an outer surface, an inner surface, a longitudinal axis, a connection opening, and a suction opening.

BACKGROUND

Dental treatments often require that emerging liquids or dissolved particles, such as saliva, spray water and blood, be suctioned off during treatment. Also, water, for example for cleaning or after using a multi-function syringe, may accrue, which has to be suctioned off. Usually, mirror suction devices are used for this purpose, which are generally formed from a tubular body of plastic, to whose end a hose is attached, which in turn is connected to a pump. The distracting liquids and solids are carried away through the hose.

A mirror suction device is often not guided and held by the attending dentist or dental surgeon himself but by an assistant, because the attending dentist has to hold a drilling tool with the one hand and a mirror with the other, with which he is able to inspect the area to be treated. The above-described procedure is disadvantageous in that the two people have to stand or sit very close to each other, around the area to be treated. Particularly if the interventions are rather difficult or demanding with regard to fine-motor skills, this may be perceived as distracting by the attending physician.

A medical mirror suction device in which the inner surface has a mirror-coated surface which is visible through the suction opening is known from DE 102006048463 A1. The reflective coating according to the disclosure enables the user to use the medical mirror suction device both as a mirror suction device for removing liquids and particles and, simultaneously, as a mirror. Using such a mirror suction device, it is now possible for them to carry out the treatment without an assisting person.

Thus, the mirror suction device is simultaneously used as a mirror suction device and as a mirror. The basic concept of the combination is very good in principle; however, the possible applications and ruggedness are limited.

SUMMARY

The present disclosure provides a mirror suction device which is improved over the known mirror suction device. The former is supposed also to offer the possibility of inspecting the oral cavity during suctioning. In particular, the mirror suction device is to be rugged and suitable for other tasks.

According to the disclosure, the aforementioned advantages are achieved by providing a mirror suction device having the features of claim 1.

According to that, the hollow base body has along its longitudinal axis a central wall, which divides the cavity at least in some portions into a first hollow channel and a second hollow channel.

Preferably, the central wall has a wall thickness which, starting from a free frontal edge, increases at first and then remains substantially constantly thick. In other words, the central wall is configured to narrow conically in the direction towards the free frontal edge, for reasons of aerodynamics.

The two hollow channels can be used for different tasks. For example, one hollow channel may have a compressed air connection through which compressed air can be blown through the suction opening including the mirror. As a result, it is possible for the dentist to blow clear the area in the oral cavity during the treatment without having to change tools. Advantageously, a valve is provided for this purpose by means of which compressed air can be added or turned off. Preferably, the valve is configured in such a way that it can be opened and closed with one finger by means of a lever. In a particularly advantageous embodiment, the hollow channel that is supposed to serve for feeding the compressed air narrows in the direction towards the suction opening.

Further, a light guide, through which light can be guided into the oral cavity, may be disposed in one of the two hollow channels. In addition or as an alternative, a data line, e.g. for a camera that is in the region of the suction opening, may also be disposed in this hollow channel. The arrangement of the guides in a hollow channel provided specifically for this purpose is advantageous because in it, they are protected against liquid and the impact of particles.

In principle, a combination is also conceivable, i.e. that the additional hollow channel both has a compressed air connection and serves for introducing compressed air, but also has a light and/or data line.

Moreover, the mirror suction device is more rugged due to the central wall. The central wall may be arranged in a continuous manner over the entire length of the mirror suction device, or just in some portions. In principle, it is possible that the central wall is visible through the suction opening or extends up to the mirror.

It was found that producing the mirror suction device is particularly simple if the mirror suction device or base body is formed from two base body parts extending substantially in the longitudinal direction along a longitudinal axis of the base body or mirror suction device. The base body parts, which can be produced independently of each other, in that case correspond to the two hollow channels. In a particularly advantageous embodiment, both base body parts have a closed channel, wherein one longitudinal side of the channel serves as the central wall in the assembled state of the two base body parts. The two base body part or hollow channels are thus attached to each other with, in each case, one longitudinal wall, so that the two longitudinal walls that are connected to each other form the central wall.

In order to reduce the costs connected to the one-off use, the mirror suction device according to the disclosure is produced as a disposable suction device from inexpensive components. In particular, an otherwise customary glass mirror is not used in that case. A metal disk, preferably comprising highly polished steel with a high-quality surface finish, a film or a reflective surface which is, for example, vapor-coated with chromium, may be used instead of the glass mirror. A paint coating is also conceivable. What is essential is that the mirror or the reflective surface used can be produced at lower costs than a customary glass mirror.

In the region of the suction opening, the base body forms a surface which is as planar as possible and is provided with a reflective material. The reflective material may be, for example, a film glued to the planar surface. Alternatively, it is possible to mirror-coat the planar surface, preferably to vapor-coat it with chromium, or to paint it with a reflective paint. Thus, production in a quick and simple manner is possible; the costs are low.

The mirror member according to the disclosure is preferably formed from either a reflective metal disk or a plastic disk provided with a reflective film or another coating applied thereto. In particular, the coating can be produced by vapor-coating, preferably with chromium.

In a particularly advantageous variant of an embodiment, the plastic disk comprises the same plastic as the rest of the base body or the rest of the base body parts. This is advantageous in that only a single material has to be procured for manufacture. Furthermore, this is advantageous for production, because production can be carried out under constant physical conditions, e.g. with respect to temperature and pressure.

For example, the base body of the mirror suction device may also be formed from two longitudinal halves, which are welded together and retain the mirror member in a groove. The mirror member, as it were, is thus disposed between the two longitudinal halves and surrounded in some portions of its outer circumference by the two longitudinal halves.

In a particularly advantageous variant of an embodiment, the mirror suction device according to the disclosure is formed from two base body parts, wherein
   the mirror member is retained in a mirror-accommodating portion of the first base body part in an opening whose inner wall forms an upper retaining shoulder abutting against an outer wall of the mirror member, wherein the upper retaining shoulder is formed by the first base body part and surrounds the entire outer circumference of the mirror member,
   the opening of the first base body part narrows from an underside of the base body in the direction towards the suction opening and has a diameter, on its side facing towards the underside of the base body, which is greater than the diameter of the mirror member,
   the two base body parts are connected to each other in a gap-free manner in such a way that, together, they integrally form the base body.

According to the disclosure, the base body may comprise components which are connected to each other, preferably welded or glued to each other, and thus ultimately form a quasi-integral mirror suction device. Within the sense of the disclosure, quasi-integral means that after production, the two base body parts can be separated from each other only destructively. If the base body comprises two base body parts, an inexpensive mirror member is also used.

An essential insight is that an attractive outer appearance of the base body is obtained when one of the two first base body parts is as large as possible and the other base body part is as small as possible and the smaller base body part extends in the longitudinal direction of the mirror suction device only to a small extent. Thus, the distracting groove or distracting burr produced by the connecting surfaces between the base body parts is relatively short.

Furthermore, it is crucial that the smaller base body part and the connection between the base body parts are disposed in a region that the attending physician does not touch at all, or only to a little extent, during the treatment. Even if the connecting surfaces have a negative effect on the surface of the mirror suction device, they do not result in a haptic distraction.

The arrangement in the region of the back of the mirror, i.e. at the underside of the mirror suction device, is particularly advantageous because this region is generally not visible during the use of the mirror suction device. Thus, variations in the surface, which cannot be felt by touch but are visible, hardly stand out in a negative way.

Thus, the first base body part forms almost the entire base body of the mirror suction device, whereas the second base body part substantially only seals the opening required for inserting the mirror into the first base body part. Relative to the outer surface, the first base body part has a percentage of the surface of 80 to 95%, and the second base body part has a percentage of the surface of 5 to 20%.

Advantageously, the mirror member is circular, but may also be oval or have other suitable shapes. The following is based on the customary circular shape of the mirror member.

In order to permanently hold the mirror member in a reliable manner, the first base body part has a mirror-accommodating portion with an opening for inserting the mirror member. Thus, the first base body part laterally surrounds the mirror inserted into the opening. In the finished mirror suction device, the opening is sealed at the back, i.e. behind the inserted mirror, by the second base body part. The two base body parts are welded or glued to each other.

The visible surface of the mirror member remains clear and is visible from the front. In an advantageous variant of an embodiment, the second base body part disposed on the back of the mirror member, as a whole, has dimensions that exceed the dimensions of the mirror member only to an insubstantial extent. It is thus possible to first produce the first base body part, then insert the mirror member from the back into the free opening in the first base body part, and finally seal the opening from the back with the second base body part.

According to the disclosure, the opening in the first base body part narrows in the direction towards a bottom surface within the base body in the region of the suction opening; it is configured and dimensioned such that the inserted mirror, in the mirror-accommodating portion, abuts against an upper retaining shoulder formed in an inner wall of the opening.

What is essential is that the opening of the mirror-accommodating portion of the first base body part is dimensioned such that the mirror member can be inserted into the mirror-accommodating portion. Therefore, the opening, on the side thereof facing towards the rear of the base body, has a diameter exceeding the diameter of the mirror member. Accordingly, the second base body part also has a diameter exceeding the diameter of the mirror member. In the vertical cross-sectional direction, the opening is ultimately a conically narrowing passage into which the mirror member is inserted from the wider side. These explanations refer to a circular basic shape of the mirror member; if the latter has a different shape, the mirror-accommodating portion has to be configured in such a manner that this other shape can also be accommodated.

In a particularly advantageous variant of an embodiment, the mirror member, in the vertical cross section, is configured to be substantially trapezoidal, wherein the diameter of the mirror member increases starting from a mirror surface in the direction towards the underside of the base body. As was already explained, the inner wall of the opening of the first base body part has a vertical cross section corresponding thereto; its diameter increases starting from the underside of the base body.

Advantageously, the trapezoidal shape of the outer wall of the mirror member and of the inner wall of the opening or the upper retaining shoulder are selected such that the visible mirror surface, in the inserted state of the mirror member, ends flush with the bottom surface of the first base bottom part surrounding the mirror surface. By abutting against the outer side of the mirror surface, the upper retaining shoulder prevents the mirror member from being able to protrude upwards over the bottom surface or become detached from the base body in that direction.

Advantageously, the mirror member is retained in a frictional or positive manner already when it is inserted into the mirror member accommodating portion. For example, the diameter of the opening can be configured to be minimally smaller than the diameter of the mirror member. In that case, the mirror member, when inserted, deforms the surrounding material, and pushes it back slightly, so that the mirror member is subsequently retained by the elastic material. Then, the second base body part is glued or molded onto the first base body part with the mirror inserted and retained therein.

Alternatively, it is also conceivable that not the entire diameter of the opening is smaller than the diameter of the mirror member, but that only several, preferably three, raised portions evenly distributed over the course of the inner wall or retaining shoulder are provided, which retain the mirror member in its position already prior to the connection with the second base body part.

The mirror surface and the surrounding bottom surface form as planar an overall surface as possible, via which the air flow, suctioned-off liquid and particles can be carried away in an optimal manner. The planar overall surface also causes the noise development due to air turbulence in this region to be low. A protrusion of the mirror member over the bottom surface of the first base body part of up to 0.3 mm is still considered to be flush in the sense of the disclosure.

As an alternative to the plain trapezoidal shape, the mirror member may have a maximum diameter, for example in the central area of its vertical cross section. Thus, the diameter first increases, starting from the mirror member surface, and then decreases again in the direction towards the back of the mirror member. The inner wall of the opening is then configured correspondingly, so that the mirror member can be snapped into the mirror-retaining groove thus formed. In that case, the inner wall of the opening not only forms an upper retaining shoulder, but also a lower retaining shoulder. It is also conceivable that the lower retaining shoulder, which the mirror member, starting from the back thereof, contacts even before its maximum diameter, is formed by the second base body part.

The second base body part can be connected to the first base body part and have a corresponding shape, in such a manner that it pushes the mirror member within the opening against the upper retaining shoulder under a bias. This ensures that the mirror member is retained securely and is unable to move even during the treatment. The inner wall of the opening serves as a sealing lip and, similar to a shaft seal ring, abuts the mirror side surface peripherally.

A thermoplastic synthetic material, such as polypropylene or also polyethylene, is particularly suitable for production. By adding additives, the outward appearance of the mirror suction device may be influenced.

The mirror member is not located in front of the suction opening, but substantially behind the suction opening in the flowing direction of the suctioned air, i.e. within the base body. It is thus achieved that the mirror suction device is not made longer by an upstream mirror, which would reduce the suctioning performance. However, the mirror member may in some portions also be disposed in front of the suction opening.

Even though gluing the base body parts together is possible in principle, it has proved to be particularly advantageous to weld the two base body parts together and not use any adhesive. The disadvantages, which adhesives generally involve, may thus be avoided.

Advantageously the first base body part can be produced and configured such that the mirror member is frictionally or positively retained in the first base body part already prior to the connection of the two base body parts. This simplifies the following production steps.

BRIEF DESCRIPTION OF THE DRAWINGS

The disclosure is explained further with reference to the following Figures. They merely show exemplary embodiments; the disclosure is not supposed to be limited thereto.

In the Figures.

DETAILED DESCRIPTION OF THE DRAWINGS

Figure 1:
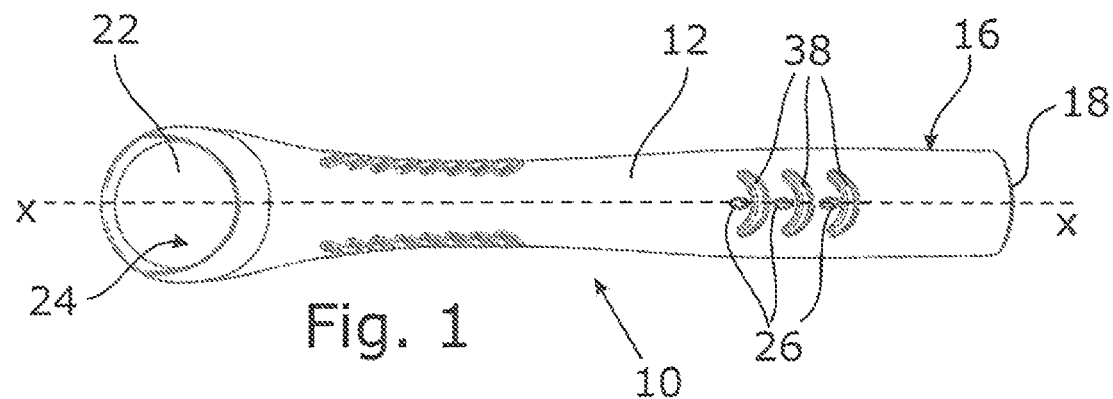
FIG. 1: shows a mirror suction device according to the disclosure from above.
Figure 2:
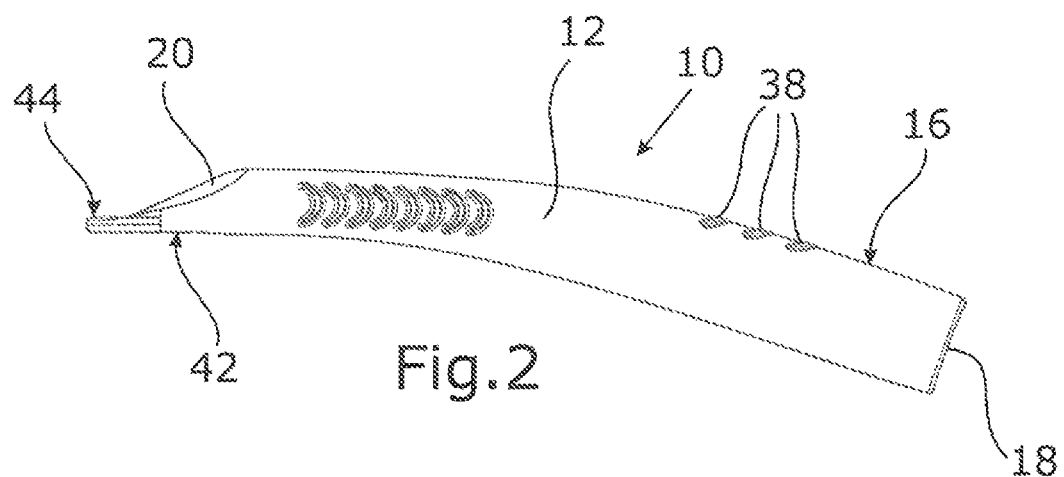
FIG. 2: shows the mirror suction device according to the disclosure of FIG. 1 from the side.
Figure 3:
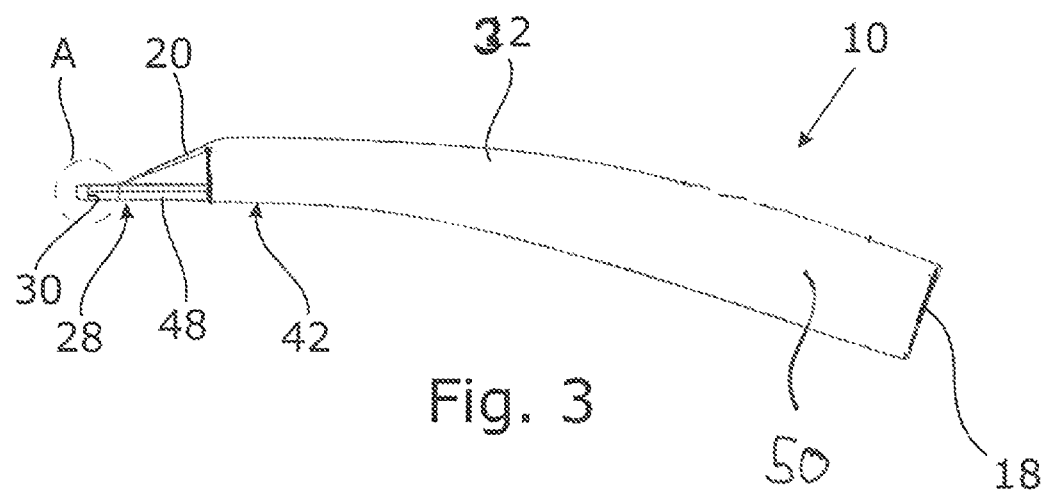
FIG. 3: shows a hollow channel from the side, looking towards a central wall.

As is apparent, in particular, from FIGS. 1 to 3, a mirror suction device 10 according to the disclosure has a hollow, tubular base body 12 with an inner surface 14 and an outer surface 16. Moreover, the base body 12 has a longitudinal axis X-X (see FIG. 1). The arc shape of the mirror suction device 10, which is recognizable particularly in FIGS. 2 and 3, is advantageous in that it is easier to guide towards the site to be treated.

The base body 12 has a connection opening 18 for a hose, which is not shown, and a suction opening 20 for suctioning particles and liquids. The liquids or particles to be suctioned off are sucked through the connection opening 20 and carried away through the connection opening 18 via the hose.

According to the disclosure, a mirror member 22, which is viewable through the suction opening 20, is disposed within the base body 12 in the region of the suction opening 20. Accordingly, a visible mirror surface 24 faces towards the suction opening 20. The mirror member 22 is disposed in its entirety within the base body 12, i.e. behind the suction opening 20 as viewed in the flowing direction of the air to be suctioned off. The suctioned air is guided over the mirror surface 24, whereby fogging of the mirror member surface 24 is effectively prevented.

The mirror member 22 according to the disclosure is preferably formed from either a reflective metal disk or a plastic disk provided with a reflective film or another coating applied thereto. In particular, the coating can be produced by evaporation, preferably with chromium.

The mirror suction device 10 may have additional openings 26 through which air is also suctioned. The additional openings 26 prevent a negative pressure within the base body 12 if the suction opening 20 is sealed by the tongue or cheek of the patient, for example. Three additional openings 26 are provided in the exemplary embodiment, however, only a single additional opening 26 or even more than three additional openings 26 are also conceivable.

Profile members 38, which provide for a safe grip of the mirror suction device 10 and prevent the fingers of the attending dentist from slipping, are discernible on the outer surface 16 of the base body 12.

Figure 6:
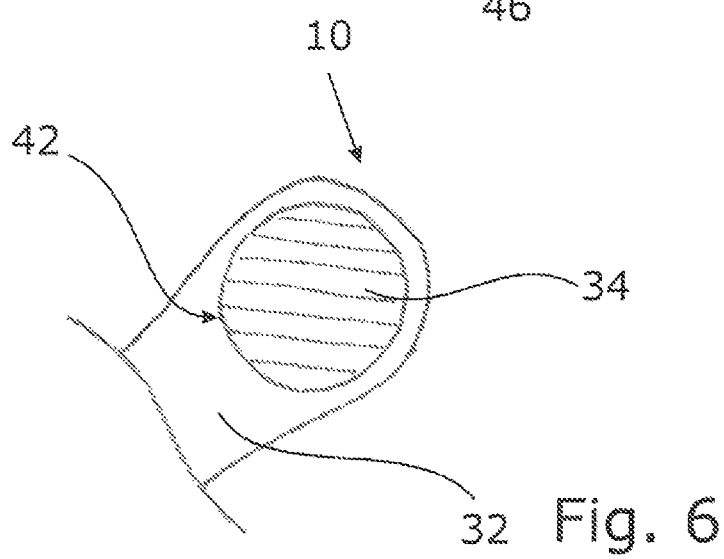
FIG. 6: shows a simplified illustration of the front region of the mirror suction device from below.

FIGS. 3 and 6 show an exemplary embodiment in which the base body 12 is formed from a first base body part 32 and a second base body part 34. A central wall 50 can also be seen in FIG. 3. The first base body part 32 has a mirror-accommodating portion 48 with an opening 28, in which the mirror member 22 is inserted in the assembled state. The central wall 50 extends up to the mirror member 22. An inner wall 30 of the opening 28 surrounds the mirror member 22 and abuts against an outer wall 36 of the mirror member 22 at least in some portions. The opening 28 narrows starting from an underside 42 of the base body in the direction towards the suction opening 20. The opening 28, on the side thereof facing towards the underside 42 of the base body, has a diameter greater than the diameter of the mirror member 22. This is required for the mirror member 22 to be insertable into the mirror-accommodating portion 48.

Figure 5:
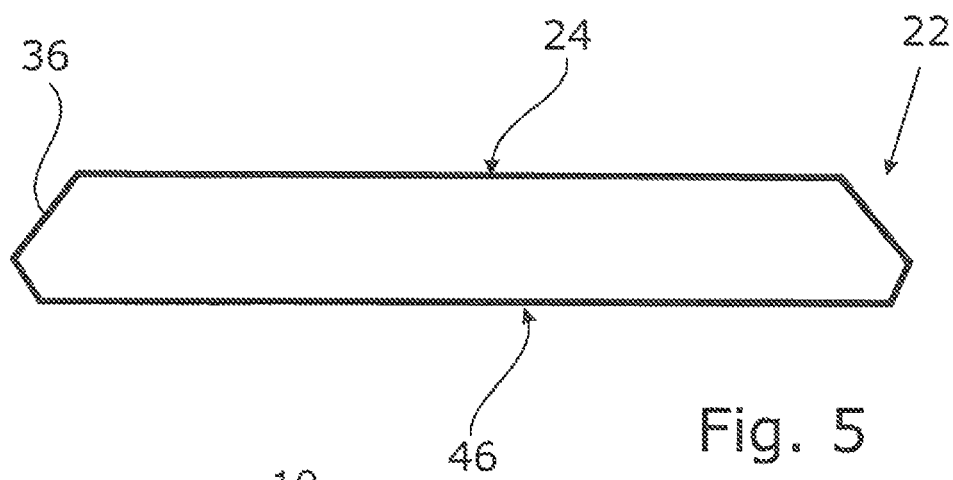

In cross section, the mirror member 22 is configured to be approximately trapezoidal at least in some portions (see FIG. 5), so that its diameter increases at least in some portions, starting from the mirror member surface 24 in the direction towards an underside of the base body 42. The mirror member 22 has a mirror back 46 facing away from the visible mirror surface 24. FIG. 5 shows an embodiment in which the mirror member 22 has a machine diameter in the vertical direction, in about the lower third. This shape simplifies the insertion or snap-in attachment in the mirror-accommodating portion 48. A lower retaining shoulder abuts against the lower region of the outer wall 36.

Figure 4:
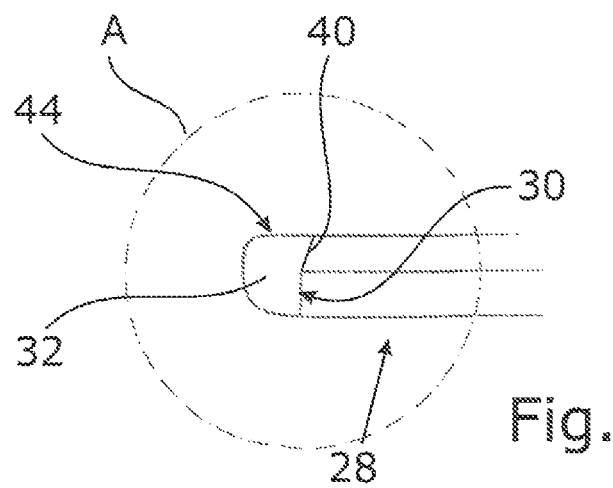
FIG. 4: shows an enlargement of the region A from FIG. 3, FIG. 5: shows a mirror in a side view.

In an enlarged illustration of the region A from FIG. 4, FIG. 4 illustrates that an upper retaining shoulder 40 surrounds the entire outer wall 36 of the mirror member 22 and seals a space next to and below the mirror member 22. The seal is improved by means of a bias of the upper retaining shoulder 40. This means that the mirror member 22, when it is inserted into the first base body part 32, is pressed against the upper retaining shoulder 40 and the latter is minimally compressed or elastically deformed.

Furthermore, this variant of an embodiment is advantageous in that the mirror member 22 is embedded almost flush into a bottom surface 44.

FIG. 6 shows the front area of the mirror suction device 10 with a view of the underside 42 of the base body. The second base body part 34 (hatched), which seals the opening 28, is visible.

The disclosure is not limited to the exemplary embodiments described, but also includes all embodiments acting in an equivalent way. The above-described variant of an embodiment is to be understood only as an example, and not as limiting. It is also possible to combine the technical features shown in any technically meaningful manner.

The invention claimed is:

1. A dental mirror suction device for suctioning liquids and particles from an oral cavity of a patient, the dental mirror suction device comprising: a tubular hollow base body having an inner surface, an outer surface, a longitudinal axis, a connection opening for a hose, and a suction opening, wherein the inner surface has a mirror-coated surface which is viewable through the suction opening and which is arranged such that the oral cavity is viewable, by means of it, at least in some portions, wherein the hollow base body has along its longitudinal axis a central wall, which divides the cavity at least in some portions into a first hollow channel and a second hollow channel, wherein a wall thickness of the central wall, starting from a free frontal edge, increases at first and then remains substantially constantly thick.

2. The dental mirror suction device according to claim 1, wherein the central wall is configured such that one of the first and second hollow channels narrows in the direction towards the suction opening and the other of the first and second hollow channels widens in the direction towards the suction opening.

3. The dental mirror suction device according to claim 2, wherein the narrowing hollow channel has a connection for compressed air.

4. The dental mirror suction device according to claim 1, wherein a light guide extends through one of the first and second hollow channels.

5. The dental mirror suction device according to claim 1, wherein at least one data line configured for a video camera configured to be disposed in the region of the suction opening, extends through one of the two hollow channels.

6. The dental mirror suction device according to claim 1, wherein the first and second hollow channels are produced independently of one another and connected to each other by means of the central wall to form the mirror suction device.

7. The dental mirror suction device according to claim 1, wherein the mirror-coated surface is configured to be approximately trapezoidal at least in some portions, so that the diameter increases at least in some portions, starting from the mirror-coated surface towards an underside of the base body.

* * * * *